(12) United States Patent
Timm

(10) Patent No.: US 9,636,147 B2
(45) Date of Patent: May 2, 2017

(54) SCREW ASSEMBLY WITH DEFORMABLE BUSHING

(71) Applicant: Alphatec Spine, Inc., Carlsbad, CA (US)

(72) Inventor: Jens Peter Timm, Carlsbad, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 227 days.

(21) Appl. No.: 14/713,826

(22) Filed: May 15, 2015

(65) Prior Publication Data

US 2015/0289907 A1    Oct. 15, 2015

Related U.S. Application Data

(62) Division of application No. 13/420,012, filed on Mar. 14, 2012, now Pat. No. 9,060,812.

(60) Provisional application No. 61/468,744, filed on Mar. 29, 2011.

(51) Int. Cl.
*A61B 17/70* (2006.01)

(52) U.S. Cl.
CPC ...... *A61B 17/7037* (2013.01); *A61B 17/7002* (2013.01); *A61B 17/7032* (2013.01); *A61B 17/7034* (2013.01); *A61B 17/7035* (2013.01)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS 7,896,902 B2 *  3/2011  Jeon .................... A61B 17/7032
                                                               606/246

* cited by examiner

*Primary Examiner* — Nicholas Woodall
(74) *Attorney, Agent, or Firm* — Dinsmore & Shohl LLP

(57) ABSTRACT

A method of securing a fixation rod to a screw assembly that includes a screw, a bushing, and a receiver includes the steps of inserting the fixation rod within a receiver portion of the bushing and the receiver, advancing a locking member into contact with an engagement surface on a proximal portion of the bushing, applying a force with the locking member to increase an amount of friction between a distal engagement surface of the bushing and a head portion of the screw, and increasing the force to deform a deformable portion of the bushing and increase an amount of friction between the fixation rod and the bushing.

18 Claims, 3 Drawing Sheets

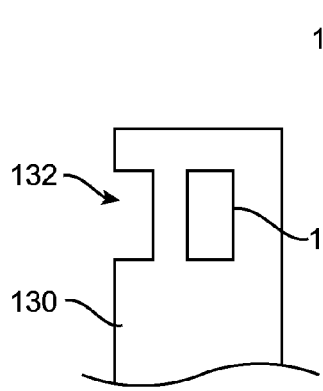
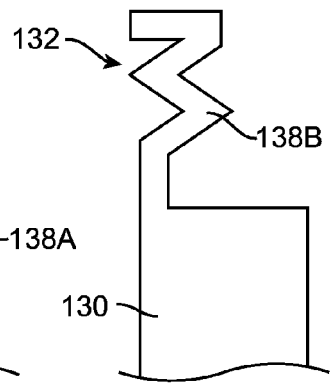
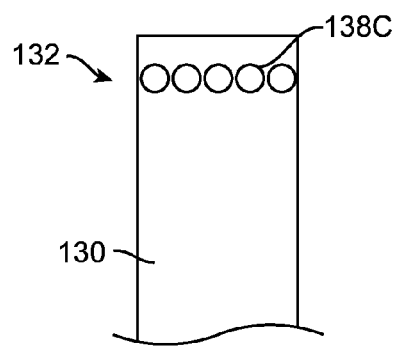
FIG. 4A  FIG. 4B  FIG. 4C
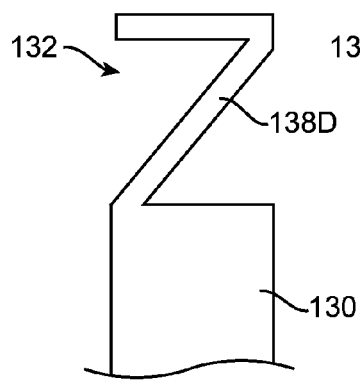
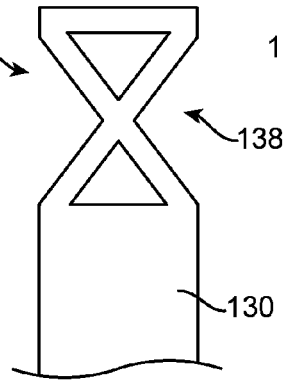
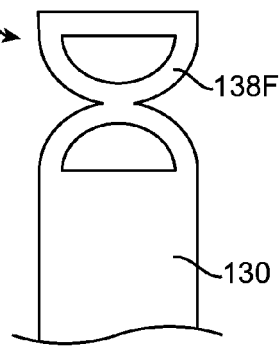
FIG. 4D  FIG. 4E  FIG. 4F
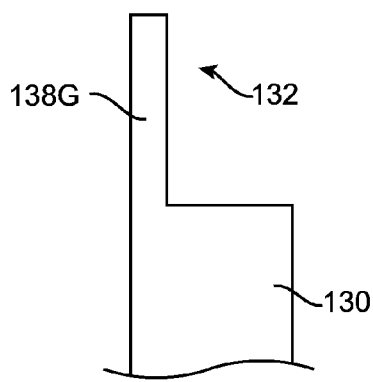
FIG. 4G

SCREW ASSEMBLY WITH DEFORMABLE BUSHING

CROSS REFERENCE TO RELATED APPLICATIONS

This application is a divisional of and claims priority from U.S. Ser. No. 13/420,012 filed on Mar. 14, 2012 and entitled "Screw Assembly with Deformable Bushing" which in turn claims priority to U.S. Provisional Application No. 61/468,744, filed Mar. 29, 2011, and both of which are incorporated herein by reference in their entirety.

FIELD

The present disclosure generally relates to the field of spinal orthopedics, and more particularly to spinal fixation systems having screw assemblies and bushings.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a bone screw with a threaded shank that is adapted to be threaded into a vertebra, and a rod receiving head, usually including a U-shaped channel. The shank and rod receiving head can be provided as a mono-axial screw, whereby the rod receiving head is fixed with respect to the shank, or a poly-axial screw, whereby the rod receiving element has free angular movement with respect to the shank. In use, the shank portion of each screw is threaded into a vertebra, and once properly positioned, a fixation rod is seated into the channel. The rod is then locked in place by tightening a set-screw, plug, or similar type of fastening mechanism into the rod receiving head.

While current spinal fixation systems have proven effective, it can be difficult to position rods within the rod receiving head of various fixation devices prior to locking the rod with the fastening mechanism. In particular, it can be difficult to align and seat a rod into the rod receiving head of a poly-axial implant since the rod receiving head has poly-axial freedom of movement with respect to the shank. More particularly, the poly-axial freedom of movement of the rod receiving head can allow the receiving head to "flop," thereby requiring the surgeon or an assistant to hold the receiving head in the desired position during rod introduction.

Accordingly, there remains a need for a poly-axial bone screw assembly in which the rod receiving head can be maintained in a desired angular orientation while the rod is positioned within the receiver head.

SUMMARY

A bushing for a bone screw assembly includes a distal portion, a receiver portion, and a proximal portion. The distal portion includes a distal engagement surface that engages with a head of a bone screw. The receiver portion receives a fixation rod. The proximal portion includes a proximal engagement surface that engages with a locking member and a deformable portion that deforms from a first configuration to a second configuration based on a force applied by the locking member.

In other features, the proximal portion includes side walls with a first height in the first configuration and a second height that is less than the first height in the second configuration. The first height is greater than a diameter of the fixation rod within the receiver portion and the second height is less than or equal to the diameter of the fixation rod.

In still other features, an amount of friction between the distal engagement surface and the head of the bone screw increases when the locking member applies a force on the proximal engagement surface in the first configuration. The proximal portion resists deformation when the force applied by the locking member is less than a first threshold force and decreases from a first height to a second height when the force applied by the locking member is greater than or equal to the first threshold force. The proximal portion decreases from the second height to a third height when the force applied by the locking member is greater than or equal to a second threshold force. The third height is less than a diameter of the fixation rod within the receiver portion. The force applied by the locking member plastically deforms the fixation rod. The deformable portion includes a structurally weakened element. The deformable portion includes side walls with at least one of windows, springs, perforations, angled members, cross-linking members, hemispherical members, and thinned side walls.

A screw assembly includes a screw, a receiver, a locking member, and a bushing. The screw includes a head portion and a threaded portion. The receiver couples to the head portion to receive a fixation rod. The locking member attaches to the receiver. The bushing is disposed between the receiver and the head portion. The bushing includes a distal portion, a receiver portion, and a proximal portion. The distal portion includes a distal engagement surface that engages with the head portion. The receiver portion secures the fixation rod. The proximal portion includes a proximal engagement surface that engages with the locking member and a deformable portion that deforms from a first configuration to a second configuration based on a force applied by the locking member.

In other features, the receiver freely pivots about the head portion in the first configuration. The fixation rod freely moves relative to the receiver and bushing in the first and second configurations. An amount of friction between the distal engagement surface and the head portion increases in the second configuration to restrict pivoting of the head portion. The deformable portion deforms to a third configuration based on the force applied by the locking member. An amount of friction between the fixation rod and bushing increases in the third configuration to restrict movement of the fixation rod.

A method of securing a fixation rod to a screw assembly including a screw, a bushing, and a receiver, includes the steps of inserting the fixation rod within a receiver portion of the bushing and the receive, advancing a locking member into contact with an engagement surface on a proximal portion of the bushing, applying a force with the locking member to increase an amount of friction between a distal engagement surface of the bushing and a head portion of the screw, and increasing the force to deform a deformable portion of the bushing and increase an amount of friction between the fixation rod and the bushing. The method further includes the step of increasing the force to deform the fixation rod.

BRIEF DESCRIPTION OF THE DRAWINGS

FIGS. 4A-4G are partial cross-sectional views of examples of deformable portions of the deformable bushing according to the principles of the present disclosure.

DETAILED DESCRIPTION

Figure 1:
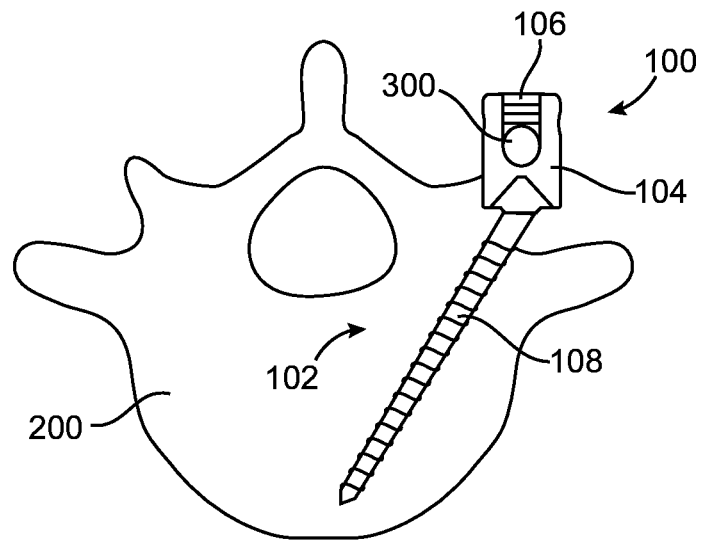
FIG. 1 is an elevational side view of a screw assembly including the deformable bushing according to the principles of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

Embodiments of the invention will now be described with reference to the Figures, wherein like numerals reflect like elements throughout. Embodiments of the invention may include several novel features, no single one of which is solely responsible for its desirable attributes or which is essential to practicing the invention described herein. The words proximal and distal are applied herein to denote specific ends of components of the instrument described herein. For example only, a proximal end refers to the end of an instrument nearer to an operator of the instrument when the instrument is being used. A distal end refers to the end of a component further from the operator and extending towards the surgical area of a patient and/or the implant. Similarly, the words left and right, top and bottom, and upper and lower may denote opposite sides of a component.

The deformable bushing of the present disclosure includes features that enable separate locking steps for rigid fixation of the receiving head of the screw assembly and the fixation rod. The bushing rests within the receiving head between a spherical head of the bone screw and the fixation rod. As a locking member, such as a setscrew, is tightened within the receiving head, the bushing is forced into contact with the spherical head and frictional forces between the bushing and the spherical head limit the poly-axial movement of the receiving head relative to the bone screw. Initially, the locking member does not contact the fixation rod, but as the locking member is tightened, the bushing begins to deform. The locking member begins to contact the fixation rod and frictional forces between the locking member, fixation rod, and the receiving head limit movement of the fixation rod relative to the receiving head. The locking member may be tightened further causing deformation of the fixation rod and rigid locking of the fixation rod and the entire screw assembly.

Referring now to FIG. 1, a screw assembly 100 according to the principles of the present disclosure may be inserted into a vertebra 200. Although the screw assembly 100 of the present disclosure may be described with reference to a poly-axial screw assembly configuration, the principles of the present disclosure may apply to other configurations, such as a mono-axial screw assembly configuration. The screw assembly 100 may be inserted into the pedicle region of the vertebra 200. Multiple screw assemblies may be inserted into adjacent vertebrae to enable attachment of a fixation rod 300. The fixation rod 300 may be rigidly attached to these instrumented vertebrae to provide a rigid fixation system for adjusting the rotation and placement of each vertebra 200. The screw assembly 100 may include a bone screw 102 for attachment to the vertebra 200, a receiving head 104 for receiving the fixation rod 300, and a locking member 106, such as a setscrew, to retain the fixation rod 300 within the receiving head 104. The bone screw 102 further includes a threaded end 108 for attachment to the vertebra 200. Each screw assembly 100 may be attached to one of several vertebrae by driving the threaded end 108 into the pedicle of the vertebra 200.

Referring now to FIGS. 2 and 3A-3D, the fixation rod 300 may be inserted within a cavity 110 of each receiving head 104. The cavity 110 may include a U-shaped channel or other configuration corresponding to the shape of the fixation rod 300. An internal thread 112 at the proximal end may be configured to receive the locking member 106. The locking member 106 may include mating threads 114 that engage the internal thread 112. The locking member 106 may be inserted into the cavity 110 and subsequently tightened to rigidly attach the fixation rod 300 to the receiving head 104. This rigid attachment of the fixation rod 300 provides rigid fixation of two or more instrumented vertebrae.

Figure 2:
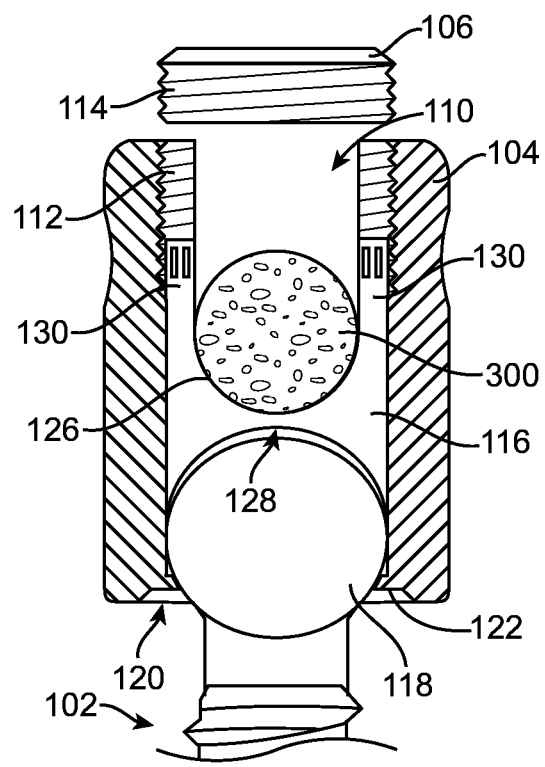
FIG. 2 is a partial cross-sectional view of the screw assembly illustrating interaction of the deformable bushing with a fixation rod and a bone screw.

Continuing now with FIG. 2, a cross-sectional view of the screw assembly 100 and fixation rod 300 reveals interaction between the fixation rod 300, a bushing 116, and a spherical head 118 of the bone screw 102. The bone screw 102 may be inserted through an aperture 120 in the cavity 110 and partially extend through the distal end of the receiving head 104. In other examples, the receiving head 104 may enable insertion of the bone screw 102 through the aperture 120 via the distal end of the receiving head 104. The aperture 120 may include a diameter that is less than the diameter of the spherical head 118 to prevent the spherical head 118 from passing completely through the aperture 120. For example, the aperture 120 may include a ridge 122 that engages with the spherical head 118.

The bushing 116 may be inserted into the proximal end of the receiving head 104 after insertion of the bone screw 102. A locking feature (not shown), such as a cam-lock, may be included to enable the receiving head 104 to retain the bushing 116. The bushing 116 may include a receiving portion such as a U-shaped channel 126 configured to receive the fixation rod 300. The channel 126 may include some curvature similar to the curvature of the fixation rod 300. For example, the channel 126 may include a radius of curvature comparable to a radius of the cross-section of the fixation rod 300. On the opposite side of the channel 126, a lower engagement surface 128 may contact the spherical head 118 of the bone screw 102. Prior to insertion of the locking member 106, the bushing 116 may rest loosely within the cavity 110 and friction forces between the spherical head 118 and the bushing 116 may be relatively low. For example, the amount of friction may be negligible and the receiving head 104 may freely rotate on the spherical head 118 of the bone screw 102. Side walls 130 extend away the channel 126 towards the proximal end of the bushing 116.

Referring now to FIGS. 3A-3D, the side walls 130 include a deformable portion 132 that enables two-step locking of the spherical head 118, receiving head 104, and fixation rod 300. Although the deformable portion 132 illustrated by the present example is formed near the proximal end of the bushing 116, one skilled in the art may appreciate that the deformable portion 132 may be located at other locations within the side wall 130. The deformable portion 132 enables the bushing 116 to include a variable height depending on the configuration of the deformable portion 132. At the proximal end of the bushing 116, the side walls 130 include an upper engagement surface 134 for engagement with the locking member 106.

Figure 3A:
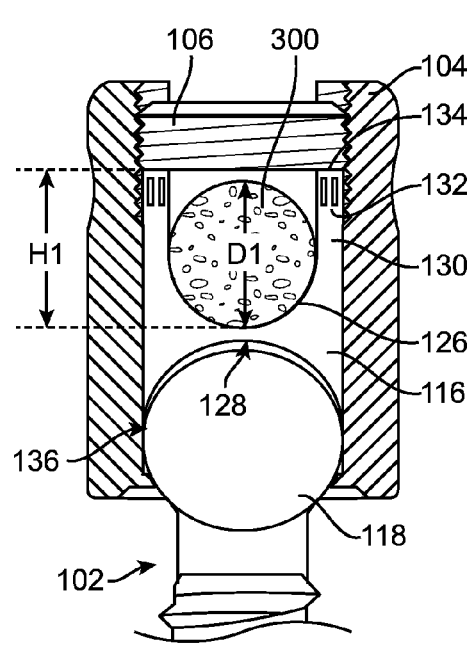
FIGS. 3A-3D are partial cross-sectional views illustrating the bushing in a non-deformed configuration and deformed configurations as a locking member advances through a receiving head of the screw assembly.

In FIG. 3A, the locking member 106 has been inserted within the receiving head 104 and the bushing 116 is in the non-deformed first configuration. The locking member 106 may be advanced to engage the upper engagement surface 134 of the bushing 116. At the opposite end of the bushing 116, contact between the lower engagement surface 128 and the spherical head 118 may be limited to an outer edge 136 of the spherical head 118. Thus, the receiving head 104 may be capable of poly-axial rotation about the spherical head 118. Friction forces between the lower engagement surface 128 and the spherical head 118 may be minimal due to the small amount of contact and associated normal forces.

In the non-deformed or first configuration, the side wall 130 of the bushing 116 may include a first height H1 measured from the upper engagement surface 134 to the apex or lowest point of the U-shaped channel 126. The fixation rod 300 may also include a diameter D1 that is less than the first height H1. When the fixation rod 300 rests in the channel 126, the upper engagement surface 134 extends above the surface of the fixation rod 300. Thus, in the first configuration, the bushing 116 prevents contact between the locking member 106 and the fixation rod 300 when the locking member 106 begins to engage with the upper engagement surface 134.

Figure 3B:
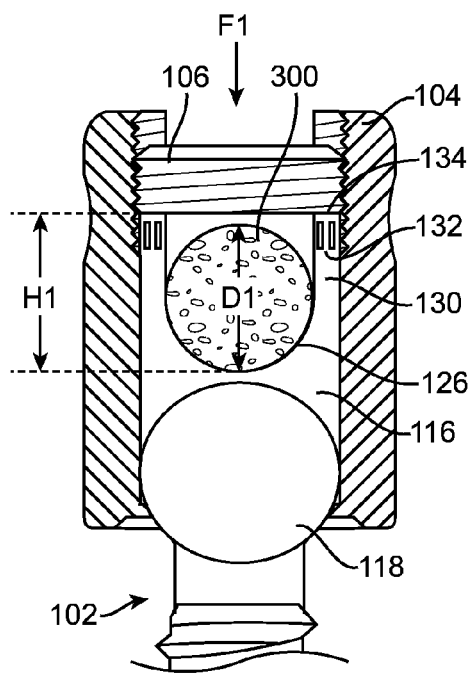

Continuing with FIG. 3B, once the locking member 106 contacts the upper engagement surface 134, the locking member 106 may be advanced further into the receiving head 104 causing the bushing 116 to move closer to the spherical head 118. The locking member 106 may apply a force to the upper engagement surface 134 that begins to move the bushing 116. Once the lower engagement surface 128 begins to contact the spherical head 118, the force may increase as the locking member 106 continues to be tightened. As the lower engagement surface 128 of the bushing 116 contacts more of the spherical head 118, the force may increase to a first force F1. The first force F1 may be sufficient to causes friction forces between the lower engagement surface 128 and the spherical head 118 that substantially limit the poly-axial movement of the receiving head 104 relative to the spherical head 118. However, with the poly-axial nature of the bone screw 102 and receiving head 104 locked, a surgeon may continue to position the fixation rod 300 within the cavity 110 because the rod diameter D1 is less than the height H1 of the side walls 130.

Figure 3C:
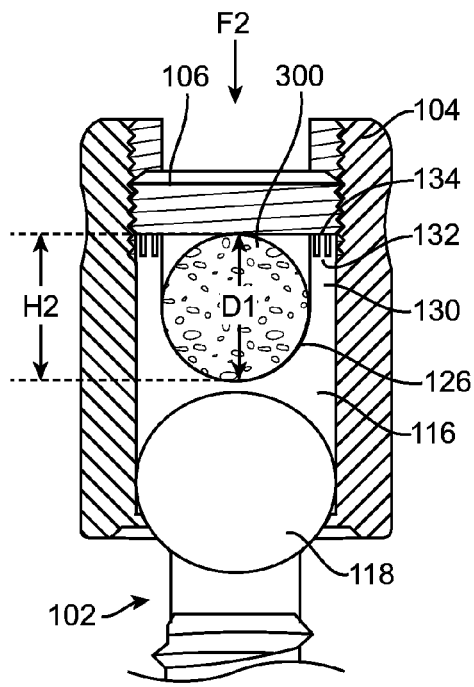

Referring now to FIG. 3C, after positioning the fixation rod 300, the locking member 106 may continue to be advanced further into the receiving head 104. The force applied by the locking member 106 on the upper engagement surface 134 may increase to a second force F2 that causes the deformable portion 132 of the bushing 116 to begin to collapse. As the deformable portion 132 collapses, the locking member 106 may also begin to contact the fixation rod 300. At that point, the height of side walls 130 of the bushing 116 may decrease to a second height H2. The second height H2 may be less than or equal to the diameter D1 of the fixation rod 300. The locking member 106 and/or channel 126 may slightly deform and friction forces between the locking member 106 and the fixation rod 300 may begin to limit movement of the fixation rod 300 relative to the receiving head 104.

Figure 3D:
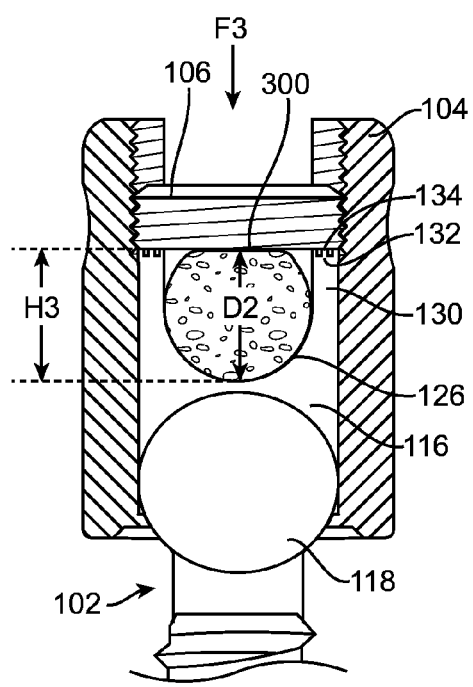

In FIG. 3D, after the locking member 106 begins to contact the fixation rod 300, the force applied by the locking member 106 may increase to a third force F3 that significantly increases the friction forces between the locking member 106 and the fixation rod 300. Furthermore, the third force F3 may be sufficient to causes a portion of the fixation rod 300 to deform. For example, the fixation rod 300 may comprise materials such as various metals including titanium and titanium allows or plastics such as polyether ether ketone (PEEK) or another plastically deformable material. The diameter of the fixation rod 300 may decrease from D1 to a second diameter D2. Similarly, the bushing 116 may continue to deform to a third height H3 that is less than the second height H2.

Referring to FIGS. 4A-4G, the deformable portion 132 may be structurally weakened by including various weakened elements (collectively 138). For example, windows 138A may pass through the side wall 130 forming apertures. Multiples windows 138A may be radially arranged around the proximal end of the bushing 116. Spring-like structures 138B may extend from the side walls 130 and may be radially arranged around the proximal end of the bushing 116. Perforations 138C may be drilled into the proximal end of the bushing 116 throughout the deformable portion 132. Various angled members 138D may extend from the side walls 130 to form the deformable portion 132. The angled members may form cross-linking members 138E. In other examples, hemispherical members 138F may be formed in the side walls 130 to enable compression of the deformable portion 132. In these and other examples, thinned walls 138G with decreased dimensions and/or geometries having greater flexibility than the solid, rigid side wall 130 may be included within deformable portion 132.

When subjected to the first force F1, the weakened elements 138 may substantially resist deformation and transfer the force to the spherical head 118, thus increasing friction forces between the spherical head 118 and the receiving head 104 and substantially locking the receiving head 104 with the spherical head 118. When subjected to the second force F2, the weakening elements 138 begin to deform, thus causing the bushing 116 to collapse from the first height H1 to the second height H2. When subjected to the third force F3, the weakening elements 138 continue to deform until the bushing 116 collapses to the third height H3, thus rigidly locking the receiving head 104, spherical head 118, and fixation rod 300 together. Thus, the deformable bushing 116 of the present disclosure permits two locking steps for rigidly securing the receiving head 104 to the bone screw 102 and the fixation rod 300 to the receiving head 104.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents. The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

The invention claimed is:

1. A method of securing a fixation rod to a screw assembly that includes a screw, a rod receiver, a bushing disposed between the rod receiver and a head of the screw, and a locking member, comprising:
   inserting the fixation rod into a receiver portion of the bushing and a cavity of the rod receiver, the fixation rod having a first diameter and the receiver portion having a sidewall with a first height greater than the first diameter;
   inserting the locking member into the cavity and into contact with an engagement surface on a proximal portion of the bushing to retain the fixation rod within the rod receiver and the bushing, in a first configuration, the sidewall maintaining the first height;
   advancing the locking member into the cavity to position the bushing into greater contact with the rod receiver and the head of the screw in a second configuration; and
   advancing the locking member into the cavity to deform the bushing and decrease the sidewall from the first height to a second height less than or equal to the first diameter in a third configuration.

2. The method of claim 1, further comprising freely positioning the rod receiver about the head of the screw in the first configuration.

3. The method of claim 1, further comprising freely positioning the fixation rod within the bushing and the rod receiver in the first configuration.

4. The method of claim 1, wherein the receiver portion maintains the first height in the first configuration.

5. The method of claim 1, wherein the receiver portion maintains the first height in the second configuration.

6. The method of claim 1, further comprising increasing a first friction force between the bushing, the rod receiver, and the head of the screw to restrict movement of the rod receiver about the head of the screw in the second configuration.

7. The method of claim 1, further comprising engaging the locking member with the fixation rod and increasing a second friction force between the locking member and the fixation rod to restrict movement of the fixation rod within the bushing and the rod receiver in the third configuration.

8. The method of claim 1, further comprising advancing the locking member into the cavity to deform the deformable portion of the bushing and decrease the sidewall from the second height to a third height in a fourth configuration.

9. The method of claim 8, further comprising increasing a first friction force between the bushing, the rod receiver, and the head of the screw to completely immobilize the rod receiver with respect to the head of the screw in the fourth configuration.

10. The method of claim 8, further comprising increasing a second friction force between the locking member and the fixation rod to completely immobilize the fixation rod within the bushing and the rod receiver in the fourth configuration.

11. A method of deforming a bushing within a bone screw assembly, comprising:
    engaging a distal engagement surface of a distal portion of the bushing with a head of a bone screw of the bone screw assembly;
    receiving a fixation rod with a diameter within a receiver portion of the bushing;
    engaging a locking member with a proximal engagement surface of the bushing; and
    advancing the locking member to apply a force that deforms a deformable portion of a sidewall of the bushing such that the sidewall decreases in height from a first height greater than the diameter of the fixation rod to a second height less than or equal to the diameter of the fixation rod.

12. The method of claim 11, further comprising increasing an amount of friction between the distal engagement surface and the head of the bone screw by applying the force on the proximal engagement surface with the locking member.

13. The method of claim 11, further comprising applying the force at a level less than a first threshold such that the locking member advances the bushing distally and the deformable portion resists deformation.

14. The method of claim 13, further comprising applying the force at a level greater than or equal to the first threshold force such that the sidewall decreases from a first height to a second height.

15. The method of claim 14, further comprising applying the force at a level greater than or equal to a second threshold force such that the side wall decreases from the second height to a third height.

16. The method of claim 15, wherein applying the force at the level greater than or equal to the second threshold force plastically deforms the fixation rod.

17. A method of securing a fixation rod to a screw assembly including a screw, a bushing, and a receiver, comprising:
    inserting the fixation rod within a receiver portion of the bushing and the receiver;
    advancing a locking member into contact with an engagement surface on a proximal portion of the bushing;
    applying a force with the locking member to increase an amount of friction between a distal engagement surface of the bushing and a head portion of the screw; and
    increasing the force to deform a deformable portion of the bushing and increase an amount of friction between the fixation rod and the bushing.

18. The method of claim 17, further comprising increasing the force to deform the fixation rod.

* * * * *